(12) United States Patent
Fowers et al.

(10) Patent No.: US 8,753,621 B2
(45) Date of Patent: *Jun. 17, 2014

(54) BAB TRIBLOCK POLYMERS HAVING IMPROVED RELEASE CHARACTERISTICS

(75) Inventors: Kirk D. Fowers, Centerville, UT (US); Ramesh C. Rathi, Cottonwood Heights, UT (US); Ai-Zhi Piao, Salt Lake City, UT (US)

(73) Assignee: Protherics Salt Lake City, Inc., Salt Lake City, UT (US)

( * ) Notice: Subject to any disclaimer, the term of this patent is extended or adjusted under 35 U.S.C. 154(b) by 353 days.

This patent is subject to a terminal disclaimer.

(21) Appl. No.: 12/886,394

(22) Filed: Sep. 20, 2010

(65) Prior Publication Data

US 2011/0070188 A1    Mar. 24, 2011

Related U.S. Application Data

(60) Provisional application No. 61/243,776, filed on Sep. 18, 2009, provisional application No. 61/275,716, filed on Oct. 16, 2009.

(51) Int. Cl.
*A61K 45/00* (2006.01)

(52) U.S. Cl.
USPC ........................................................ 424/85.2

(58) Field of Classification Search
USPC ........................................................ 424/85.2
See application file for complete search history.

(56) References Cited

U.S. PATENT DOCUMENTS

| | | | |
|---|---|---|---|
| 5,702,717 | A | 12/1997 | Cha et al. |
| 6,004,573 | A | 12/1999 | Rathi et al. |
| 6,117,949 | A | 9/2000 | Rathi et al. |
| 6,201,072 | B1 | 3/2001 | Rathi et al. |
| 6,589,549 | B2 | 7/2003 | Shih et al. |
| 7,018,645 | B1 | 3/2006 | Piao et al. |
| 7,135,190 | B2 | 11/2006 | Piao et al. |
| 2004/0185101 | A1 | 9/2004 | Shih et al. |

FOREIGN PATENT DOCUMENTS

| | | |
|---|---|---|
| CN | 1916050 | 2/2007 |
| CN | 1958074 | 5/2007 |

OTHER PUBLICATIONS

Quizlet (hormones flashcard, http://quizlet.com/10214395/hormones-flash-cards).*
International Search Report and Written Opinion of PCT/US2010/49530 mailed Mar. 29, 2012.
International Search Report and Written Opinion of PCT/US2010/49530 mailed Nov. 15, 2010.
He, el al., "In Situ Gelling Stimuli-Sensitive Block Copolymer Hydrogels for Drug Delivery", Journal of Controlled Release 127 (2008), pp. 189-207.
Hwang, et al., 'Caprolacionic Poloxamer Analog: PEG-PCL-PEG Biomacromolecules 6, (2005), pp. 885- 890.
Jeong et al., "Thermosensitive Sol-Gel Reversible Hydrogels," Advanced Drug Delivery Reviews 54 (2002), pp. 37-53.
Jeong et al., "Biodegradable Block Copolymers as Injectable Drug-Delivery Systems", Nature, vol. 388, pp. 860-862, Aug. 1997.
Jiang et al., "Injectable Hydrogels of Poly(E-caprolactone-co-glycolide)-poly (ethylene glycol)-poly(E- Caprolactone-co-glycolide) Triblock Copolymer Aqueous Solutions", Science Direct, Polymer 48 (2007), pp. 4786-4792.
Jiang et al., "Effect of Microstructures on the Phase Transition Behavior of P(CL-GL)-PEG-P(CL-GL) Triblock Copolymer Aqueous Solutions," Wiley InterScience, 29 (2008), pp. 1264-1268.
Jiang et al., "Thermogelling Hydrogels of Poly(E-Caprolactone-co-D,L-lactide)- Poly(Elhylene glycol)- Poly(E-caprolactone-co-D,L-lactide) and Poly(E-Caprolactone-co-L -lactide) -Poly(ethylene glycol)-Poly(E- Caprolactone-co-L-lactidel Aaueous Solutions," Wilev InterScience, vol. 45, (2007), pp. 4091-4099.
Jiang et al., Biodegradable and Thermoreversible hydrogels of Poly-(ethylene glycol)- Poly(E- Caprolactone-Co-Glycolide)-Poly(Ehtylene Glycol) Aqueous Solutions,' Wiley InterScience. 87A (2008), pp. 45-51.
Yu, et al., 'Injectable Hydrogels as Unique Biomedical Material,' Chemical Society Review, 37, (2008), pp. 1473-1481.

* cited by examiner

*Primary Examiner* — David J Blanchard
*Assistant Examiner* — Devang Thakor
(74) *Attorney, Agent, or Firm* — Hunton & Williams LLP (57) ABSTRACT

Improved biodegradable and bioabsorbable BAB-block copolymers exhibiting reverse thermal gellation properties, and aqueous polymer compositions including the BAB-block copolymers, are provided. Methods of making the improved BAB-block copolymers and compositions including the same are also provided.

22 Claims, 2 Drawing Sheets

BAB TRIBLOCK POLYMERS HAVING IMPROVED RELEASE CHARACTERISTICS

CROSS-REFERENCE

The subject application claims benefit of Provisional Application No. 61/243,776 filed Sep. 18, 2009 and claims benefit of Provisional Application No. 61/275,716 filed Oct. 16, 2009, which was converted from application Ser. No. 12/580,747 filed Oct. 16, 2009.

BACKGROUND OF THE INVENTION (a) Field of the Invention

The present invention relates to biodegradable and bioabsorbable BAB-block copolymers that exhibit reverse thermal gellation properties upon exposure to elevated temperatures, such as upon exposure to body temperature just prior to or upon administration. The disclosed polymers are advantageously used, for example, in the parenteral administration of drugs.

(b) Description of the Related Art

Biodegradable block copolymers exhibiting reverse thermal gellation are disclosed in U.S. Pat. Nos. 6,201,072; 6,117,949; and 6,004,573 to Rathi et al. and 5,702,717 to Cha et al., each of which is incorporated by reference herein. These polymer compositions exist as a liquid solution at low temperatures, then reversibly form gels at physiologically relevant temperatures, and provide good drug release characteristics. These compositions include biodegradable ABA- or BAB-type block copolymers having a weight average molecular weight of between about 2000 and 4990, and include about 51 to 83% by weight of an hydrophobic A polymer block comprising a biodegradable polyester and about 17 to 49% by weight of a hydrophilic B polymer block comprised of polyethylene glycol. The U.S. Pat. Nos. 7,018,645 and 7,135,190 to Piao et al., disclose mixtures of triblock copolymers exhibiting similar reverse thermal gellation properties.

The Rathi patents disclose BAB-block copolymers having reverse thermal gellation properties. According to the '949 Patent, BAB triblock copolymers were synthesized using the same PEG B-block at either end (Mw=550) but varying the poly(lactide) and/or poly(glycolide) content. The PEG and PLGA were coupled to each other via ester, urethane, or a combination of ester and urethane links. The prior BAB-block copolymers described in the Rathi patents had a weight average molecular weight $M_w$ ranging from 2000 to 4990. The following table lists characteristics of the BAB triblock copolymers disclosed in the Rathi patents:

| BAB Block Copolymers with Reverse Thermal Gellation Properties | | | |
| --- | --- | --- | --- |
| GPC Weight Average Molecular Weight | Weight % A-Blocks | PLA:PGA (mole ratio) | Reverse Thermal Gellation |
| 4140 | 70 | 78:22 | Yes |
| 4270 | 72 | 78:22 | Yes |
| 4580 | 73 | 78:22 | Yes |
| 4510 | 73 | 72:28 | Yes |

All of the PEG-PLGA-PEG triblock copolymers listed in the above table possessed reverse thermal gelation properties. The sol/gel transition temperatures for the above triblock polymers were 36, 34, 30 and 26° C. respectively. While the Rathi patents demonstrated good drug release characteristics for ABA-triblock copolymers having a weight average molecular weight $M_w$ in the range of 2000-4990 Daltons, the Rathi patents did not characterize the release characteristics of the disclosed BAB-triblock copolymers. Additionally, release characteristics were not investigated with respect to hydrophilic compounds. It has been found that the release characteristics of prior triblock copolymer compositions for hydrophilic active agents are not suitable for many controlled release applications.

SUMMARY OF THE PRESENT INVENTION

Novel reconstitutable BAB-triblock copolymers exhibiting reverse thermal gellation properties and having an improved drug release characteristics, particularly for hydrophilic active agents, have been developed. It has been surprisingly found that the BAB-triblock copolymers of the present invention are advantageous relative to ABA-triblock copolymers for providing a controlled release thermoreversible polymeric composition, particularly those exhibiting desirable release characteristics when used with hydrophilic active agents. The inventors have also found that increasing the ratio of PLG/PEG and increasing the molecular weight of BAB-block copolymers relative to known BAB-block copolymer compositions has a dramatic effect on the drug release characteristics of the BAB-block copolymer, particularly in the case of hydrophilic active agents. Prior work with respect to ABA and BAB triblocks suggested that the release characteristics for both polymers would be similar, and that the same range of triblock molecular weight would be suitable for BAB as well as ABA triblock copolymers. However, the inventors have surprisingly found that the triblock molecular weight range for controlled release thermoreversible BAB-triblock compositions differ from that which was effective for ABA-triblock copolymers.

It is an object of the present invention to provide low molecular weight triblock copolymer drug delivery systems that are biodegradable, exhibit reverse thermal gelation behavior, namely, exist as a liquid solution at low temperatures, reversibly form gels at physiologically relevant temperatures, and provide improved drug release characteristics relative to prior BAB- and ABA-triblock copolymers.

Yet another object of this invention is to provide a method for the parenteral administration of drugs in a biodegradable polymeric matrix resulting in the formation of a gel depot within the body, from which the drugs are released, such that the polymers exhibit improved drug release characteristics relative to prior BAB- and ABA-triblock copolymers.

A further object of this invention is to provide a drug delivery system for the parenteral or intratumoral administration of hydrophilic and hydrophobic drugs, peptide and protein drugs, hormones, genes/nucleic acids, oligonucleotides and anti-cancer agents. Classes of anti-cancer agents include, for example, alkylating agents, antimetabolites, antibiotics, hormonal agents, anti-vascularization or nitrosureas.

These and other objects may be accomplished by means of a BAB-block copolymer, said block copolymer comprising: i) about 60 to 85% by weight of a biodegradable, hydrophobic A-block comprising a biodegradable polyester; and ii) about 15 to 40% by weight of a biodegradable, hydrophilic B-block comprising a polyethylene glycol, wherein the weight average molecular weight of each B-block is between 300 and 1000 Daltons, wherein the BAB-block copolymer has a Mw ranging from 5000 to 8000, and is capable of exhibiting reverse thermal gellation properties when formed in an aqueous polymer solution. Preferably, the block copolymer has an A-block content that ranges from 65 to 80% and the B-block content of the copolymer ranges from 20 to 35%, and more preferably, the block copolymer has an A-block content that ranges from 67 to 75% and a B-block content that ranges from 25 to 33%. The number average molecular weight $M_n$ of the block copolymer preferably ranges from 3800 to 5000 Daltons, and more preferably from 4000 to 4600 Daltons.

These and other objects may be accomplished by means of an aqueous BAB-block copolymer composition, said composition comprising: i) about 60 to 85% by weight of a biodegradable, hydrophobic A-block comprising a biodegradable polyester; and ii) about 15 to 40% by weight of a biodegradable, hydrophilic B-block comprising a polyethylene glycol, wherein the weight average molecular weight of each B-block is between 300 and 1000 Daltons; wherein the BAB-block copolymer composition has a Mw ranging from 5000 to 8000, and exhibits reverse thermal gellation properties. Preferably, the block copolymer has an A-block content that ranges from 65 to 80% and the B-block content of the copolymer ranges from 20 to 35%, and more preferably, the block copolymer has an A-block content that ranges from 67 to 75% and a B-block content that ranges from 25 to 33%. The number average molecular weight $M_n$ of the block copolymer preferably ranges from 3800 to 5000 Daltons, and more preferably from 4000 to 4600 Daltons.

These and other objects may be accomplished by means of a method for the administration of at least one drug to a warm blooded animal in a controlled release form which comprises: (1) providing an aqueous BAB-block copolymer composition comprising: i) about 60 to 85% by weight of a biodegradable, hydrophobic A-block comprising a biodegradable polyester; and ii) about 15 to 40% by weight of a biodegradable, hydrophilic B-block comprising a polyethylene glycol, wherein the weight average molecular weight of each B-block is between 300 and 1000 Daltons; wherein the BAB-block copolymer composition has a Mw ranging from 5000 to 8000, and exhibits reverse thermal gellation properties; and (2) administering said composition to a warm blooded animal. Preferably, the block copolymer has an A-block content that ranges from 65 to 80% and the B-block content of the copolymer ranges from 20 to 35%, and more preferably, the block copolymer has an A-block content that ranges from 67 to 75% and a B-block content that ranges from 25 to 33%. The number average molecular weight $M_n$ of the block copolymer preferably ranges from 3800 to 5000 Daltons, and more preferably from 4000 to 4600 Daltons.

These and other objects may be accomplished by means of a method of making a BAB-block copolymer composition which comprises: (1) providing a BAB-block copolymer composition comprising: i) about 60 to 85% by weight of a biodegradable, hydrophobic A-block comprising a biodegradable polyester; and ii) about 15 to 40% by weight of a biodegradable, hydrophilic B-block comprising a polyethylene glycol, wherein the weight average molecular weight of each B-block is between 300 and 1000 Daltons; wherein the BAB-block copolymer composition has a Mw ranging from 5000 to 8000, and is capable of exhibiting reverse thermal gellation properties when formed in an aqueous polymer solution; and (2) freeze drying said block copolymer, wherein the block copolymer capable of exhibiting reference thermal gellation when formed as an aqueous polymer solution. Preferably, the block copolymer has an A-block content that ranges from 65 to 80% and the B-block content of the copolymer ranges from 20 to 35%, and more preferably, the block copolymer has an A-block content that ranges from 67 to 75% and a B-block content that ranges from 25 to 33%. The number average molecular weight $M_n$ of the block copolymer preferably ranges from 3800 to 5000 Daltons, and more preferably from 4000 to 4600 Daltons.

DETAILED DESCRIPTION OF THE PREFERRED EMBODIMENTS

Additional objects and advantages of this invention will become apparent from the following summary and detailed description of the various embodiments of this invention. As used herein, the following terms shall have the assigned meanings:

"Parenteral" shall include intramuscular, intraperitoneal, intra-abdominal, subcutaneous, intratumoral, intracranial (or into the resected tumor cavity), intraarticular, intrathecal, intramedular, ocular, and, to the extent feasible, intravenous and intraarterial.

"Gelation temperature" means the temperature at which the biodegradable block copolymer undergoes reverse thermal gelation, i.e. the temperature below which the block copolymer is soluble in water and above which the block copolymer undergoes phase transition to increase in viscosity or to form a semi-solid gel.

The terms "gelation temperature" and "reverse thermal gelation temperature" or the like shall be used interchangeably in referring to the gelation temperature.

"Polymer solution," "aqueous solution" and the like, when used in reference to a biodegradable block copolymer contained in such solution, shall mean a water based solution having such block copolymer dissolved therein at a functional concentration, and maintained at a temperature below the gelation temperature of the block copolymer.

Polyethylene glycol (PEG) is also sometimes referred to as poly(ethylene oxide) (PEO) or poly(oxyethylene) and the terms can be used interchangeably for the purposes of this invention.

"Reverse thermal gelation" is the phenomena whereby a solution of a block copolymer spontaneously increases in viscosity, and in many instances transforms into a semisolid gel, as the temperature of the solution is increased above the gelation temperature of the copolymer. For the purposes of the invention, the term "gel" includes both the semisolid gel state and the high viscosity state that exists above the gelation temperature. When cooled below the gelation temperature, the gel spontaneously reverses to reform the lower viscosity solution. This cycling between the solution and the gel may be repeated ad infinitum because the solution/gel transition does not involve any change in the chemical composition of the polymer system. All interactions to create the gel are physical in nature and do not involve the formation or breaking of covalent bonds.

"Drug delivery liquid" or "drug delivery liquid having reverse thermal gelation properties" shall mean a polymer solution that contains drug (the drug per se can either be dissolved or colloidal) suitable for administration to a warm-blooded animal which forms a gelled drug depot when the temperature is raised to or above the gelation temperature of the block copolymer.

"Depot" means a drug delivery liquid following administration to a warm-blooded animal which has formed a gel upon the temperature being raised to or above the gelation temperature.

"Gel" means the semi-solid phase that spontaneously occurs as the temperature of the "polymer solution" or "drug delivery liquid" is raised to or above the gelation temperature of the block copolymer. In certain situations, the formed gel may lose or absorb water from the surrounding environment to become more compact or swollen, such gels also fall within the scope of the invention.

"Aqueous polymer composition" means either a drug delivery liquid or a gel comprised of the water phase having uniformly contained therein a drug and the biodegradable block copolymer. At temperatures below the gelation temperature the copolymer may be soluble in the water phase and the composition will be a solution. At temperatures at or above the gelation temperature the copolymer will solidify to form a gel with the water phase, and the composition will be a gel or semi-solid.

"Biodegradable" means that the block copolymer can chemically break down or degrade within the body to form nontoxic components. The rate of degradation can be the same or different from the rate of drug release.

"Drug" shall mean any organic or inorganic compound or substance having bioactivity and adapted or used for a therapeutic purpose. Proteins, hormones, anti-cancer agents, oligonucleotides, DNA, RNA and gene therapies are included under the broader definition of drug.

"Peptide," "polypeptide," "oligopeptide" and "protein" shall be used interchangeably when referring to peptide or protein drugs and shall not be limited as to any particular molecular weight, peptide sequence or length, field of bioactivity or therapeutic use unless specifically stated. Such therapeutic uses may include, for example, alkylating agents, antimetabolites, antibiotics, hormonal agents, antivascularization or nitrosureas.

"Biodegradable polyesters" refer to any biodegradable polyesters, which are preferably synthesized from at least one of D,L-lactide, D-lactide, L-lactide, D,L-lactic acid, D-lactic acid, L-lactic acid, glycolide, glycolic acid, $\epsilon$-caprolactone, $\epsilon$-hydroxy hexonoic acid, $\gamma$-butyrolactone, $\gamma$-hydroxy butyric acid, $\delta$-valerolactone, $\delta$-hydroxy valeric acid, hydrooxybutyric acids, malic acid, or copolymers thereof.

BAB-type block copolymers may be synthesized by ring opening polymerization, or condensation polymerization according to reaction schemes disclosed in U.S. Pat. Nos. 5,702,717; 6,004,573; and 6,117,949, hereby fully incorporated by reference to form a monofunctional diblock (MeO-PEG-PLG) followed by coupling of two diblock copolymers of same or different molecular weight using. For example, the ester or urethane linkage to yield a BAB triblock (MeO-PEG-PLG-PEG-OMe) copolymer. In other instances, the monofunctional B(PEG) blocks may be coupled to each end of the A block (polyesters) by ester or urethane links and the like. Alternatively, BAB-type block copolymers may also be prepared by reacting the difunctional hydrophobic A block at either end with ethyleneoxide. Condensation polymerization and ring opening polymerization procedures may be utilized as may the coupling of a monofunctional hydrophilic B block to either end of a difunctional hydrophobic A block in the presence of coupling agents such as isocyanates. Furthermore, coupling reactions may follow activation of functional groups with activating agents such as carbonyl diimidazole, succinic anhydride, N-Hydroxy succinimide and p-nitrophenyl chloroformate and the like.

The hydrophilic B-block is formed from PEG of appropriate molecular weights. PEG was chosen as the hydrophilic, water-soluble block because of its unique biocompatibility, nontoxicity, hydrophilicity, solubilization properties, and rapid clearance from a patient's body. In a preferred embodiment, the PEG component can be chosen from a mixture of PEGs having different average molecular weights. The hydrophobic A-blocks are utilized because of their biodegradable, biocompatible, and solubilizing properties. The in vitro and in vivo degradation of these hydrophobic, biodegradable polyester A-blocks is well understood and the degradation products are naturally occurring (or have properties that are equivalent to naturally occurring products) or biocompatible compounds that are readily metabolized and/or eliminated by the patient's body.

The concentration at which the block copolymers are soluble at temperatures below the gelation temperature may be considered as the functional concentration. Generally speaking, block copolymer concentrations of as low as 3% and up to about 50% by weight can be used and still be functional. However, concentrations in the range of about 5 to 40% are preferred and concentrations in the range of about 10-35% by weight are most preferred. In order to obtain a viable gel phase transition with the copolymer, a certain minimum concentration, e.g. 3% by weight, is required. At the lower functional concentration ranges, the formed gel will be weak and may result in phase separation. Where the polymer concentrations are higher, a more stronger gel network may be formed.

The mixture of the biodegradable copolymer and peptide/protein drugs, and/or other types of drugs, may be prepared as an aqueous solution of the copolymer below the gelation temperature to form a drug delivery liquid where the drug may be either partially or completely dissolved. When the drug is partially dissolved, or when the drug is essentially insoluble, the drug exists in a colloidal state such as a suspension or emulsion. The disclosed polymers are advantageously used in the parenteral administration such as intramsclular or subcutaneous, intratumoral, intracranial (or into the resected tumor cavity), intraarticular, intrathecal, intramedullary, ocular, topical, transdermal, vaginal, buccal, transmucosal, pulmonary, transurethral, rectal, nasal, oral, or aural administration, whereupon the polymers will undergo a reversible thermal gelation since body temperature will be above the gelation temperature.

This system will cause minimal toxicity and minimal mechanical irritation to the surrounding tissue due to the biocompatibility of the materials, pliability of the gel, and the precise control of the swelling characteristics in physiological areas where swelling would result in damage to the surrounding tissue. The polyester blocks in the system will further be completely biodegraded to lactic acid, glycolic acid, and other corresponding monomers within a specific time interval. The polyethylene glycol blocks are removed from the body by excretion. The drug release, gel strength, gelation temperature and degradation rate can be controlled by proper design and preparation of the various copolymer blocks, namely, through modifications of the weight percent of A-blocks and B-blocks, the mole percentages lactate and glycolate, and the molecular weight and polydispersity of the BAB block copolymers. Drug release is also controllable through adjustment of the concentration of polymer in the drug delivery liquid.

A dosage form comprised of a solution of the block copolymer that contains either dissolved drug or drug as a suspension or emulsion is administered to the body. This formulation then spontaneously gels, due to the reverse thermal gelation properties of the block copolymer, to form a drug depot as the temperature of the formulation rises to body temperature. The only limitation as to how much drug can be loaded into the formulation is one of functionality. Namely, the drug load may be increased until the thermal gelation properties of the copolymer are adversely affected to an unacceptable degree, the drug release properties are altered adversely, or until the properties of the formulation are adversely affected to such a degree as to make administration of the formulation unacceptably difficult. Generally speaking, it is anticipated that in most instances the drug will make up between about 0.01 to 20% by weight of the formulation with ranges of between about 0.01 to 10% being highly common. These ranges of drug loading are not limiting to the invention. Provided functionality is maintained, drug loadings outside of these ranges fall within the scope of the invention.

A distinct advantage to the compositions described herein lies in the ability of the block copolymer to increase the solubility of many drug substances. The combination of the hydrophobic A-block(s) and hydrophilic B-block(s) renders the block copolymer amphiphilic with distinct hydrophilic and hydrophobic domains which stabilize and solubilize hydrophobic drugs. In that regard, it functions much as a soap or surfactant in having both hydrophilic and hydrophobic properties. While prior ABA triblock copolymers were found to be particularly advantageous in solubilizing hydrophobic or poorly water soluble drugs, such as paclitaxel, the release characteristics of these ABA triblock copolymers for hydrophilic compounds has been found to be inadequate for many controlled release applications.

Figure 1:
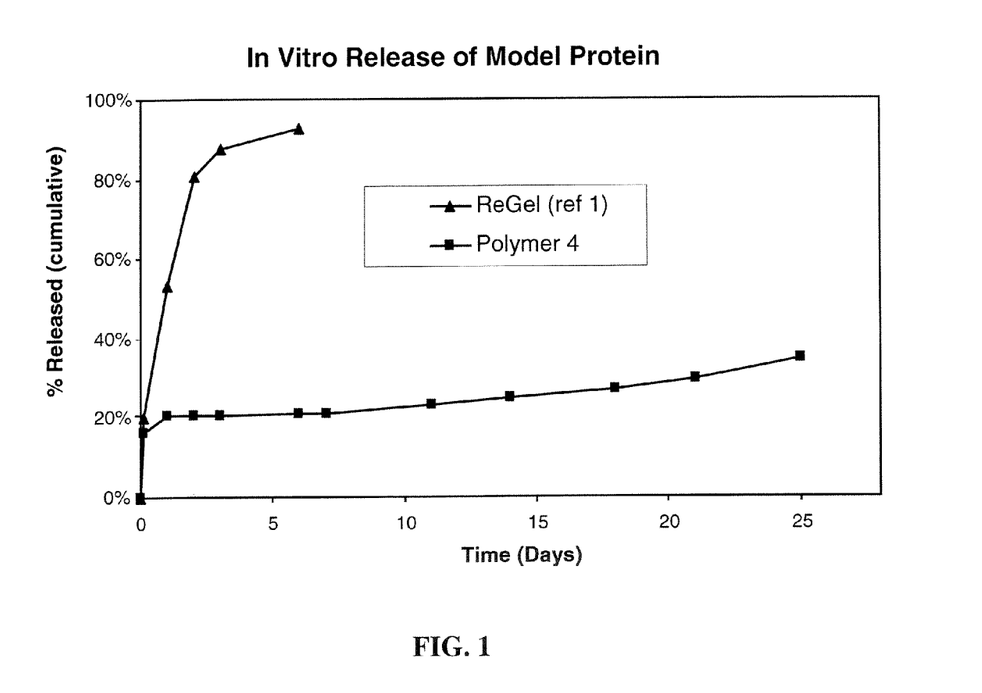
FIG. 1 compares the release profile of polymer composition of the example with an ABA-block copolymer ReGel.

It has been surprisingly found that the BAB-triblock copolymers of the present invention are advantageous relative to ABA-triblock copolymers for providing a controlled-release thermoreversible polymeric composition, particularly with respect to hydrophilic active agents. The release characteristics of the BAB-triblock copolymers of the present invention were investigated with respect to bovine serum albumin (BSA), which is a model protein for predicting the controlled release behavior of numerous hydrophilic proteins and other hydrophilic active agents. As shown in FIG. 1, the prior art ABA-triblock copolymer, ReGel, releases approximately 95% of the BSA within the first five days. In contrast, a BAB-triblock (Composition No. 4, Table 1) exhibited sustained release of the BSA over periods exceeding twenty-five days. The data in FIG. 1 demonstrates that BAB-triblock copolymers are advantageous for controlled release of hydrophilic molecules, including proteins such as BSA, over extended periods of time.

The inventors have also found that increasing the ratio of PLG/PEG and increasing the molecular weight of BAB-block copolymers relative to known BAB-block copolymer compositions has a dramatic effect on the drug release characteristics of the BAB-block copolymer, particularly in the case of hydrophilic active agents. Prior work with respect to ABA and BAB triblocks suggested that the release characteristics for both polymers would be similar, and that the same range of triblock molecular weight would be suitable for BAB as well as ABA triblock copolymers. The release characteristics of BAB-triblock copolymers were investigated with respect to an exemplary hydrophilic macromolecule, dextran (M.W. 70,000 Daltons). The inventors surprisingly found that when the ratio of PLG/PEG and the total molecular weight was increased in the BAB-triblocks above levels that were previously describes as being adequate, desirable controlled release characteristics for hydrophilic active agents were obtained.

According to a particularly preferred aspect of the invention, the following hydrophilic bioactive agents are expected to be particularly suitable for use in combination with the BAB-block copolymers of the present invention based on their hydrophilic characteristics: Oxytocin, vasopressin, adrenocorticotropic hormone, epidermal growth factor, platelet-derived growth factor (PDGF), pigment epithelial derived factor (PEDF) prolactin, luliberin, luteinizing hormone releasing hormone (LHRH), LHRH agonists, LHRH antagonists, growth hormones (human, porcine, bovine, etc.), growth hormone releasing factor, insulin, erythropoietin, somatostatin, glucagon, interleukins [interleukin-2 (IL-2), interleukin-11 (IL-11)], interferons (interferon-$\alpha$, $\beta$, or $\gamma$), gastrins (tetragastrin, pentagastrin, urogastrone), secretin, calcitonin, enkephalins, immunoglobulins, endorphins, angiotensins, thyrotropin releasing hormone (TRH), tumor necrosis factors (TNF), nerve growth factors (NGF), granulocyte-colony stimulating factor (G-CSF), granulocyte macrophage-colony stimulating factor (GM-CSF), macrophage-colony stimulating factor (M-CSF), heparinase, hANP, glucagon-like peptide (GLP-1), bone morphogenic proteins (BMP), antibodies and fragments thereof, enzymes, cytokines, vaccines, goserelin, rapamycin, rituximab, renin, bradykinin, bacitracins, polymyxins, colistins, tyrocidine, gramicidins, cyclosporins and synthetic analogues, modifications and pharmacologically active fragments thereof.

In certain situations the drug loaded polymer may be administered in the gel state instead of as a solution. The gelation may be the result of raising the temperature of a drug laden polymer solution to above the gelation temperature of the polymer prior to administration, or may be caused by raising the concentration of the polymer in the solution to above the saturation concentration at the temperature of administration, or may be caused by addition of additives to the polymer solution which causes the solution to gel. In any event, the gel thus formed may be administered in parenteral administration such as intramusclular or subcutaneous, intratumoral, intracranial (or into the resected tumor cavity), intraarticular, intrathecal, intramedullary, ocular, topical, transdermal, vaginal, buccal, transmucosal, pulmonary, transurethral, rectal, nasal, oral, or aural administration of drugs.

This invention is applicable to bioactive agents and drugs of all types including nucleic acids, hormones, anticancer-agents, and it offers an unusually effective way to deliver polypeptides and proteins. Many labile peptide and protein drugs are amenable to formulation into the block copolymers of the invention and can benefit from the reverse thermal gelation process described herein. While not specifically limited to the following, examples of pharmaceutically useful polypeptides and proteins may be erythropoietin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-$\alpha$, $\beta$, or $\gamma$, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, cyclosporins or synthetic analogues, modifications and pharmacologically active fragments thereof, enzymes, cytokines, antibodies or vaccines.

The only limitation to the polypeptide or protein drug which may be utilized is one of functionality. In some instances, the functionality or physical stability of polypeptides and proteins can also be increased by addition of various additives to the BAB block copolymers of the invention either before or after forming into polymer drug composition. Additives can also be added to aqueous solutions or suspensions of the polypeptide or protein drug. Additives, such as polyols (including sugars), amino acids, surfactants, polymers, other proteins and certain salts may be used in connection with stabilizing the drugs themselves without altering the properties of the drug delivery composition. These additives can be readily incorporated into the block copolymers which will remain functional with reverse thermal gelation properties.

Developments in protein engineering may provide the possibility of increasing the inherent stability of peptides or proteins. While such resultant engineered or modified proteins may be regarded as new entities in regards to regulatory implications that does not alter their suitability for use in the present invention. One of the typical examples of modification is PEGylation where the stability of the polypeptide drugs can be significantly improved by covalently conjugating water-soluble polymers, such as polyethylene glycol, with the polypeptide. Another example is the modification of the amino acid sequence in terms of the identity or location of one or more amino acid residues by terminal and/or internal addition, deletion or substitution. Any improvement in stability enables a therapeutically effective polypeptide or protein to be continuously released over a prolonged period of time following a single administration of the drug delivery liquid to a patient.

In addition to the previously listed peptide or protein based drugs, other drugs from all therapeutic and medically useful categories may be utilized. These drugs are described in such well-known literature references as the Merck Index, the Physicians Desk Reference, and The Pharmacological Basis of Therapeutics. A brief listing of specific agents is provided for illustration purposes only, and shall not be deemed as limiting: anti-cancer agents such as actinomycin D, anastrozole, azacitidine, bevacizumab, bicalutamide, bleomycin, BCNU, bortezomib, camptothecin, capecitabine, carboplatin, cetuximab, daunorubicin, dasatinib, docetaxel, doxorubicin, epirubicin, erlotinib, exemestane, gefitinib, gemcitabine, goserelin, imatinib, STI-571, irinotecan, lapatinib, letrozole, leuprolide, methotrexate, mitomycin, oxaliplatin, paclitaxel, pemetrexed, rituximab, sorafenib, sunitinib, tamoxifen, taxotere, tegafur-uracil, temozolomide, trastuzumab, triptorelin, vinorelbine; antipsychotics such as olanzapine and ziprasidone; antibacterials such as cefoxitin; anthelmintics such as ivermectin; antivirals such as acyclovir; immunosuppressants such as cyclosporin A (cyclic polypeptide-type agent), steroids, and prostaglandins. Additional anti-cancer agents include porcabazine, dacarbazine, altretamine, displatin, mercaptopurine, thioguanine, fludarabine phosphate, cladribine, pentostatin, fluorouracil, cytarabine, azacitidine, vinblastine, vincristine, etoposide, teniposide, topotecan, dactinomycin, idarubincin, plicamycin, flutamide, leuprolide, gasoerelin, aminoglutethimide, amsacrine, hydroxyurea, asparaginase, mitoxantrone, mitotane, retinoic acid derivative, bone marrow growth factors amifostine, carmustine, lomustine, semustine, anti-VEGF, etc.

As mentioned above, the present invention involves BAB-triblock copolymers exhibiting improved drug release characteristics relative to known BAB-triblock copolymers. It is been surprisingly found that for BAB-block copolymers, increasing the ratio of PLG/PEG and increasing the molecular weight of the BAB-block copolymer has a dramatic effect on the drug release characteristics of the block copolymer, specifically with regard to hydrophilic compounds. In order to illustrate preferred embodiments of this invention, the synthesis of various BAB-triblock copolymers were completed. The following are examples that illustrate preferred embodiments of the invention but are intended as being representative only.

EXAMPLE 1

Synthesis of MeO-PEG-PLG-PEG-OMe Polymer
(PLG/PEG=2.6, L/G=72/28)

Monomethoxy polyethylene glycol (MeO-PEG, Mw 550; 50 g) was added to 350 ml of toluene and dried by azeotropic distillation to remove the residual water. The final volume of toluene in the reaction mixture was approximately 200 ml. The reaction flask was cooled to 90° C. and DL-Lactide (98.99 g) followed by glycolide (31.01 g) were added. After DL-Lactide and glycolide dissolved, the stannous octoate (~126 mg) was added drop wise to start the polymerization. The reaction mixture was refluxed for 20-22 hours at 130° C. The reaction flask was cooled to 60° C. and hexamethyl diisocyanate HMDI (7.65 g) was added and the reaction mixture was heated for 18-20 hours at 60° C. followed by additional heating at 130° C. for 6 hours. The toluene (~100 ml) was distilled off and the reaction mixture was precipitated in to 1400 ml of anhydrous diethyl ether. The diethyl ether was decanted off, the residue was dissolved in methylene chloride (60 ml), and the polymer was precipitated in to 1000 ml of anhydrous diethyl ether. The diethyl ether was decanted off and the residual solvents were removed under vacuum at 80-90° C. using the rotary evaporator. Finally, the product was dried under vacuum (<1 mm of mercury) at 140° C. for 5 hours to yield 162 g of MeO-PEG-PLG-PEG-OMe polymer.

Purification of BAB Polymer

BAB polymer was further purified by dissolving in water at a concentration of approximately 20% (w/w) followed by precipitation at 70-80° C. The supernatant was decanted off and the equivalent amount of water was added to the precipitated polymer mixture. The polymer was dissolved and precipitated again at 70-80° C. Finally, the precipitated polymer was dissolved in minimum amount of water and freeze-dried to obtain the pure polymer.

Analysis Methods

Weight average molecular weights and number average molecular weights were determined by GPC (gel permeation chromatography) and NMR, respectively. The lactide/glycolide ratios were calculated from NMR data. GPC analysis was performed on a combination of Phenogel, mixed bed, and Phenogel, 500 Angstrom columns calibrated with PEG standards using RI detection and tetrahydrofuran as the eluent. NMR spectra were taken in $CDCl_3$ on a Bruker 200 MHz instrument.

EXAMPLE 2

Following the general procedure outlined in Examples 1, BAB type of block copolymers with different hydrophobic to hydrophilic ratios were synthesized (Table I). Composition of various BAB polymers synthesized is shown in Table I. All of the synthesized block copolymers (MeO-PEG-PLG-PEG-OMe) possessed reversible thermal gelation properties.

TABLE I

| | Synthesis composition | | | | | Gelation | |
|---|---|---|---|---|---|---|---|
| No. | MeO-PEG Mw | PLG/PEG (w/w) | Lactide (mole %) | Glycolide (mole %) | Mn (by NMR) | Mw (by GPC) | temp. (Tgel) | RTG* |
| 1 | 550 | 2.36 | 72.0 | 28 | 3640 | 4611 | 28.5 | Yes |
| 2 | 550 | 2.45 | 72.0 | 28 | 3889 | 4951 | 30.5 | Yes |
| 3 | 550 | 2.50 | 72.0 | 28 | 3941 | 5658 | 27.1 | Yes |
| 4 | 550 | 2.60 | 72.0 | 28 | 4044 | 5911 | 30.1 | Yes |
| 5 | 550 | 2.70 | 72.0 | 28 | 4334 | 6510 | 30.7 | Yes |

*RTG = Reverse thermal gelation.

EXAMPLE 3

This example illustrates the release profile of bovine serum albumin (a model protein) from BAB triblock [MeO-PEG-(DL-lactide-co-glycolide)-PEG-OMe] polymer gel in vitro. FITC-labled bovine serum albumin was dissolved in a BAB triblock copolymer (Example 4 of Table 1) aqueous solution at a concentration of 5 mg/ml. The concentration of BAB polymer in the final mixture was 30% (w/w). For in vitro release test, a 0.25 gm sample of this mixture was put into a vial and equilibrated at 37° C. Since the temperature was greater than the gelation temperature of the copolymer, a gel formed on the bottom of vial. Once the gel was formed, 5 ml of PBS (phosphate buffered saline, pH 7.4) was added to the vial. The vials were closed and placed into an incubator at 37° C. The release study was performed in triplicate. Samples were collected periodically during the release study. Release buffer was exchanged with the fresh buffer at each time point. The released protein content in the samples was analyzed by fluorescence microplate reader. The results are presented in FIG. 1.

FIG. 1 compares the release profile of a BAB-triblock according to the present invention (Composition No. 4 of Table 1) with that of a known ABA-triblock for bovine serum albumin (BSA), a model protein used to predict the release characteristics of hydrophilic proteins and other hydrophilic active agents. The ABA-triblock used for comparative purposes is ReGel, which is disclosed by Rathi et al. in U.S. Pat. Nos. 6,201,072; 6,117,949; and 6,004,573. As shown in FIG. 1, the prior art ABA-triblock copolymer ReGel releases approximately 95% of BSA within the first five days. In contrast, the BAB-triblock copolymer (Composition No. 4 of Table 1) of the present invention exhibits sustained release of the BSA over periods exceeding twenty-five days. The data in FIG. 1 demonstrates that BAB-triblock copolymers are advantageous for controlled release of hydrophilic molecules, including proteins such as BSA, over extended periods of time.

EXAMPLE 4

This example illustrates the effect of BAB triblock copolymer composition on the release profile of dextran (70 kDa, a model macromolecule). FITC-labled dextran was dissolved in various BAB triblock copolymers (Examples 1, 2 and 4 of Table 1) aqueous solution at a concentration of 5 mg/ml. The concentration of BAB polymer in the final mixture was 30% (w/w). The release study was performed at 37° C. as described in Example 3 and the samples were analyzed by fluorescence microplate reader. The results are presented in FIG. 2.

Figure 2:
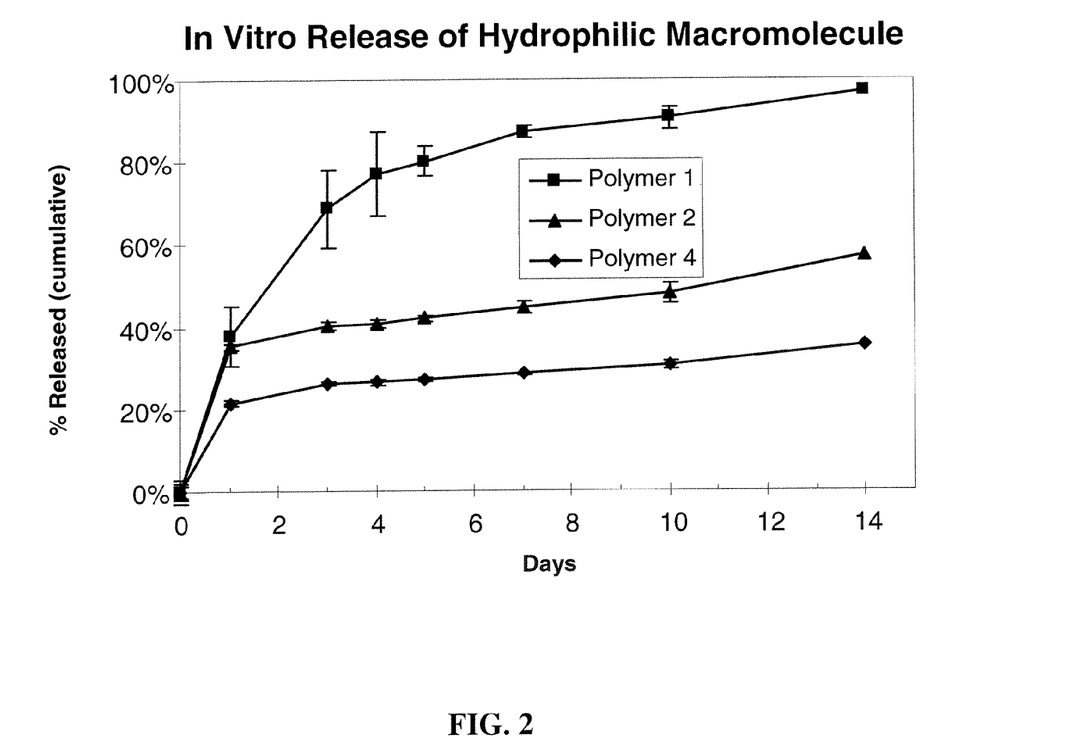
FIG. 2 compares the release of a hydrophilic macromolecule by BAB-block copolymer compositions of the examples.

FIG. 2 compares the release profile of BAB-triblock copolymers having different ratios of PLG/PEG for an exemplary hydrophilic macromolecule dextran (M.W. 70,000 Daltons). The inventors have unexpectedly found that increasing the ratio of PLG/PEG and increasing the molecular weight of BAB-block copolymers relative to known BAB-block copolymer compositions has a dramatic effect on the drug release characteristics of the BAB-block copolymer, particularly in the case of hydrophilic active agents. As shown in FIG. 2, the BAB-triblock copolymer having a ratio of PLG/PEG of 2.36 had released over 90% of the dextran over a period of ten days, whereas a BAB-triblock copolymers having PLG/PEG ratios of 2.45 and 2.60 had released less than 45% and less than 25%, respectively, over the same time period. Thus, the data in FIG. 2 demonstrates that BAB-triblock copolymers according to the invention have improved release characteristics, particularly for hydrophilic agents.

The above description will enable one skilled in the art to make BAB type block copolymers that form aqueous solutions having reverse thermal gelation properties and to utilize the same in the field of drug delivery. Although the controlled delivery of protein is illustrated in the examples to show the functionality of hydrogels formed from aqueous solutions of block copolymers, these descriptions are not intended to be an exhaustive statement of all drugs which can be utilized and loaded into the biodegradable block copolymers. Certainly, numerous other drugs from various classes of therapeutic agents are well suited for delivery from aqueous compositions of block copolymers as described herein. Neither are all block copolymers which may be prepared, and which demonstrate the critical reverse thermal gelation property, are specifically shown. However, it will be immediately apparent to one skilled in the art that various modifications may be made without departing from the scope of the invention which is limited only by the following claims and their functional equivalents.

The invention claimed is:

1. A BAB-block copolymer comprising:
   (i) about 60 to 85% by weight of a biodegradable, hydrophobic A-block comprising a biodegradable polyester; and
   (ii) about 15 to 40% by weight of a biodegradable, hydrophilic B-block comprising a polyethylene glycol, wherein the weight average molecular weight of each B-block is between 300 and 1000 Daltons; wherein the BAB-block copolymer has a Mw ranging from 5000 to 8000 Daltons and the ratio of A-block to B-block is 2.45 to 2.70, and is capable of exhibiting reverse thermal gellation properties when formed in an aqueous polymer solution.

2. The block copolymer of claim 1, wherein the A-block content of the copolymer ranges from 65 to 80% and the B-block content of the copolymer ranges from 20 to 35%.

3. The block copolymer of claim 1, wherein the A-block content of the copolymer ranges from 67 to 75% and the B-block content of the copolymer ranges from 25 to 33%.

4. The block copolymer of claim 1, wherein the biodegradable polyester comprises residues of D,L-lactide, D-lactide, L-lactide, D,L-lactic acid, D-lactic acid, L-lactic acid, glycolide, glycolic acid, ε-caprolactone, E-hydroxy hexonoic acid, γ-butyrolactone, γ-hydroxy butyric acid, δ-valerolactone, δ-hydroxy valeric acid, hydrooxybutyric acids, or malic acid.

5. The block copolymer of claim 1, wherein the biodegradable polyester comprises residues of D,L-lactide, D-lactide, L-lactide, D,L-lactic acid, D-lactic acid, L-lactic acid, glycolide, glycolic acid, or ε-hydroxy hexonoic acid.

6. A block copolymer composition comprising the block copolymer of claim 1 and a drug.

7. The block copolymer composition of claim 6, wherein said drug is a polypeptide or protein, nucleic acid or gene, hormone, anti-cancer or anti-cell proliferation agent.

8. The block copolymer composition of claim 7, wherein said polypeptide or protein is oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone, growth hormone releasing factor, insulin, erythropoietin, somatostatin, glucagon, interleukin-2 (1L-2), interferon calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, and cyclosporins.

9. The block copolymer of claim 7, wherein said polypeptide or protein is an enzyme, cytokine, antibody or vaccine.

10. The block copolymer of claim 7, wherein said polypeptide or protein is erythropoietin, luteinizing hormone releasing hormone (LHRH), LHRH agonists, LHRH antagonists, growth hormones, tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), glucagon-like peptide (GLP-1), interleukin-11 (IL-11), and cyclosporins.

11. The block copolymer of claim 6, wherein the drug is hydrophilic.

12. The block copolymer of claim 6, wherein the drug is Oxytocin, vasopressin, adrenocorticotropic hormone, epidermal growth factor, platelet derived growth factor (PDGF), pigment epithelial derived factor (PEDF) prolactin, luliberin, luteinizing hormone releasing hormone (LHRH), LHRH agonists, LHRH antagonists, growth hormones, growth hormone releasing factor, insulin, erythropoietin, somatostatin, glucagon, interleukins, interferons, gastrins, secretin, calcitonin, enkephalins, immunoglobulins, endorphins, angiotensins, thyrotropin releasing hormone (TRH), tumor necrosis factors (TNF), nerve growth factors (NGF), granulocyte-colony stimulating factor (G-CSF), granulocyte macrophage-colony stimulating factor (GM-CSF), macrophage-colony stimulating factor (M-CSF), heparinase, hANP, glucagon-like peptide (GLP-1), bone morphogenic proteins (BMP), antibodies and fragments thereof, enzymes, cytokines, vaccines, goserelin, rapamycin, rituximab, renin, bradykinin, bacitracins, polymyxins, colistins, tyrocidine, gramicidins, and cyclosporins.

13. The block copolymer of claim 6, wherein said drug is an anti-cancer agent comprising actinomycin D, anastrozole, azacitidine, bevacizumab, bicalutamide, bleomycin, BCNU, bortezomib, camptothecin, capecitabine, carboplatin, cetuximab, daunorubicin, dasatinib, docetaxel, doxorubicin, liposomal, epirubicin, erlotinib, exemestane, gefitinib, gemcitabine, goserelin, imatinib, STI-571, irinotecan, lapatinib, letrozole, leuprolide, methotrexate, mitomycin, oxaliplatin, paclitaxel, pemetrexed, rituximab, sorafenib, sunitinib, tamoxifen, taxotere, tegafur-uracil, temozolomide, trastuzumab, triptorelin, vinorelbine, porcabazine, dacarbazine, altretamine, displatin, mercaptopurine, thioguanine, fludarabine phosphate, cladribine, pentostatin, fluorouracil, cytarabine, azacitidine, vinblastine, vincristine, etoposide, teniposide, topotecan, dactinomycin, idarubincin, plicamycin, flutamide, leuprolide, gasoerelin, aminoglutethimide, amsacrine, hydroxyurea, asparaginase, mitoxantrone, mitotane, retinoic acid derivative, amifostine, carmustine, lomustine, semustine, and anti-VEGF.

14. The block copolymer of claim 6, wherein said drug is an anti-cancer agent comprising mitomycin, bleomycin, BCNU, carboplatin, doxorubicin, daunorubicin, methotrexate, paclitaxel, taxotere, actinomycin D, and camptothecin.

15. The block copolymer of claim 6, wherein the drug content of said composition is between about 0.01 and 20% by weight.

16. The block copolymer of claim 1, wherein the number average molecular weight ranges from 3800 to 5000 Daltons.

17. The block copolymer of claim 1, wherein the weight average molecular weight ranges from 5000 to 7000 Daltons.

18. A BAB-block copolymer comprising:
(i) about 60 to 85% by weight of a biodegradable, hydrophobic A-block comprising a biodegradable polyester; and
(ii) about 15 to 40% by weight of a biodegradable, hydrophilic B-block comprising a polyethylene glycol, wherein the weight average molecular weight of each B-block is between 300 and 1000 Daltons;
wherein the BAB-block copolymer has a Mn greater than 3800 and the ratio of A-block to B-block is 2.45 to 2.70, and is capable of exhibiting reverse thermal gellation properties when formed in an aqueous polymer solution.

19. An aqueous BAB-block copolymer composition comprising:
(i) about 60 to 85% by weight of a biodegradable, hydrophobic A-block comprising a biodegradable polyester; and
(ii) about 15 to 40% by weight of a biodegradable, hydrophilic B-block comprising a polyethylene glycol, wherein the weight average molecular weight of each B-block is between 300 and 1000 Daltons;
wherein the BAB-block copolymer composition has a Mw ranging from 5000 to 8000 and the ratio of A-block to B-block is 2.45 to 2.70, and exhibits reverse thermal gellation properties.

20. An aqueous BAB-block copolymer composition comprising:
(i) about 60 to 85% by weight of a biodegradable, hydrophobic A-block comprising a biodegradable polyester; and
(ii) about 15 to 40% by weight of a biodegradable, hydrophilic B-block comprising a polyethylene glycol, wherein the weight average molecular weight of each B-block is between 300 and 1000 Daltons;
wherein the BAB-block copolymer composition has a Mn greater than 3800 and the ratio of A-block to B-block is 2.45 to 2.70, and exhibits reverse thermal gellation properties.

21. A method for the administration of at least one drug to a warm blooded animal in a controlled release form which comprises:
- (1) providing a composition comprising the aqueous BAB-block copolymer of claim 1; and
- (2) administering said composition to a warm blooded animal.

22. A method of making a BAB-block copolymer composition which comprises:
- (1) providing the BAB-block copolymer composition of claim 1; and
- (2) freeze drying said block copolymer, wherein the wherein the block copolymer is capable of exhibiting reference thermal gellation when formed as an aqueous polymer solution.

* * * * *